United States Patent [19]

Higuchi

[11] Patent Number: 4,740,309

[45] Date of Patent: Apr. 26, 1988

[54] METHODS AND APPARATUS FOR DETERMINING THE RATE OF MOVEMENT OF A STUDY SUBSTANCE THROUGH A MEMBRANE

[75] Inventor: Takeru Higuchi, Lawrence, Kans.

[73] Assignee: IPRX, Inc., Lawrence, Kans.

[21] Appl. No.: 901,659

[22] Filed: Aug. 29, 1986

[51] Int. Cl.⁴ .............................................. B01D 13/00
[52] U.S. Cl. ................................. 210/644; 210/321.63
[58] Field of Search ........................ 210/85, 96.2, 34.2, 210/644, 649; 73/64.3

[56] References Cited

U.S. PATENT DOCUMENTS 3,757,947  9/1973  Wakefield et al. .......... 210/321.2 X
4,594,884  6/1986  Bohdi et al. ................. 210/321.2 X

*Primary Examiner*—Frank Spear
*Attorney, Agent, or Firm*—Burns, Doane, Swecker & Mathis

[57] ABSTRACT

A diffusion cell for use in determining the absorption rate of a study substance through a permeable membrane. The cell includes a receptor chamber which contains receptor fluid to receive study substance absorbed through the membrane. The receptor chamber includes a fluid inlet and a fluid outlet. A rotary stirrer is situated adjacent the fluid outlet. The stirrer is rotated so as to rotate the receptor fluid in the receptor chamber in such manner that the fluid pressure is greater at the outlet than at the inlet, so that the stirrer defines a pump which pumps receptor fluid outwardly through the outlet, then through a detector, and then back into the receptor chamber through the inlet. The detector determines the concentration of study substance within the receptor fluid.

27 Claims, 2 Drawing Sheets

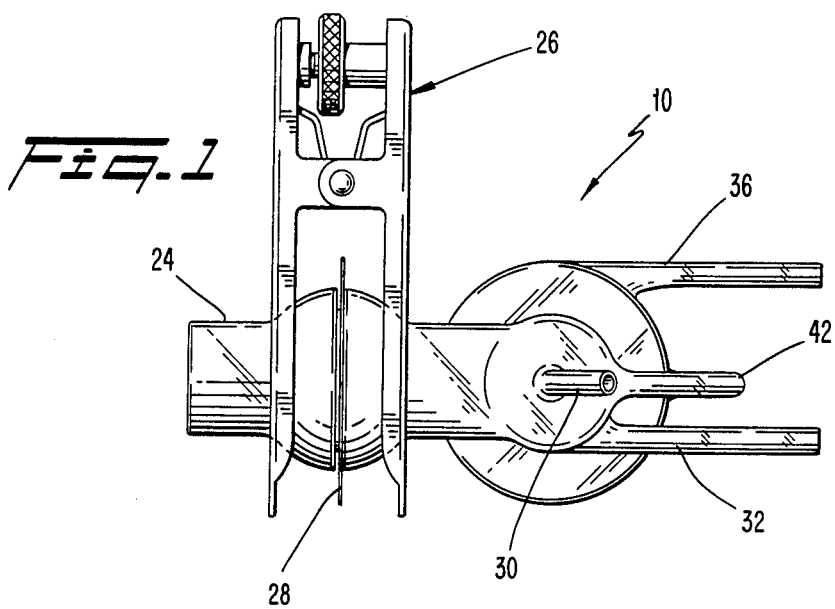
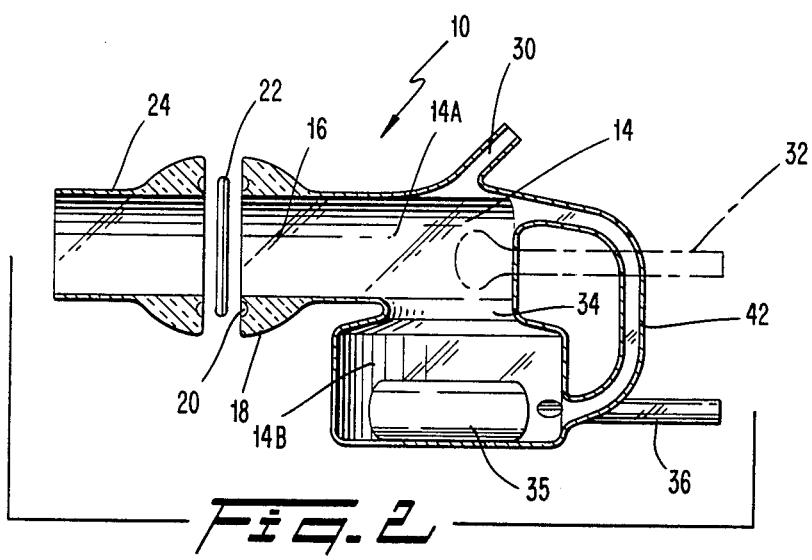
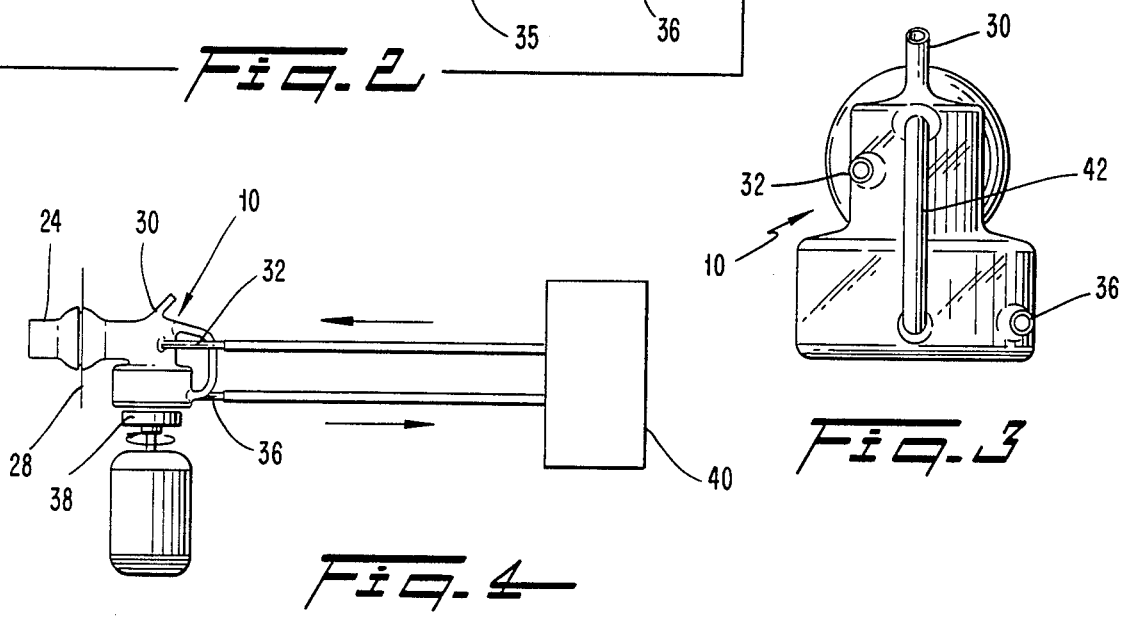

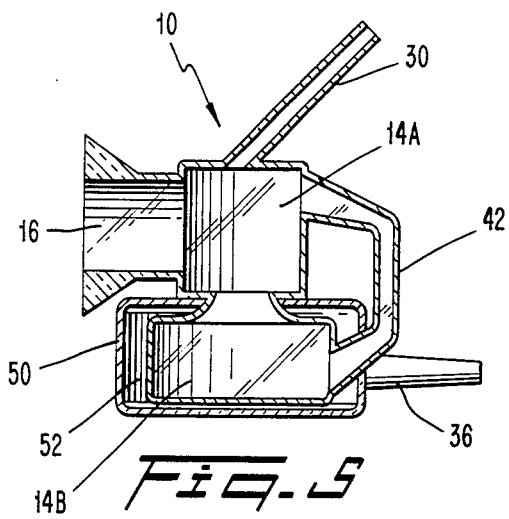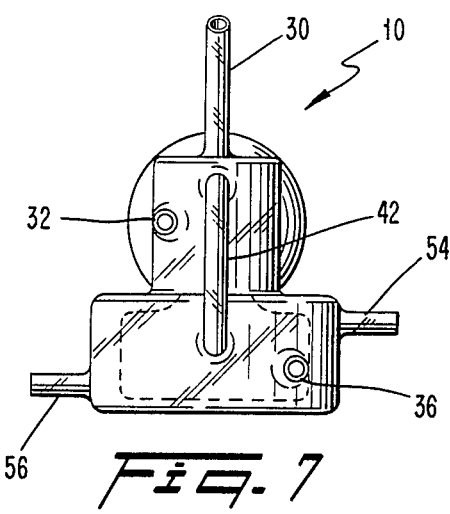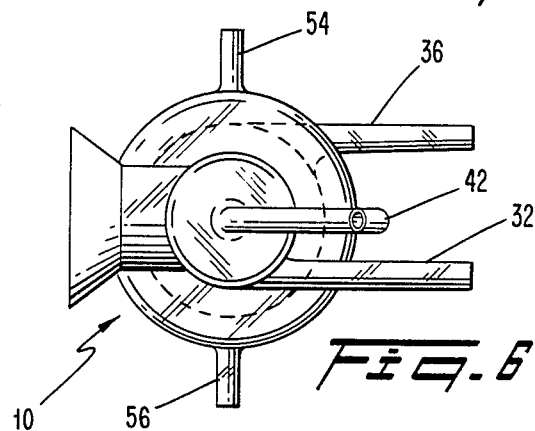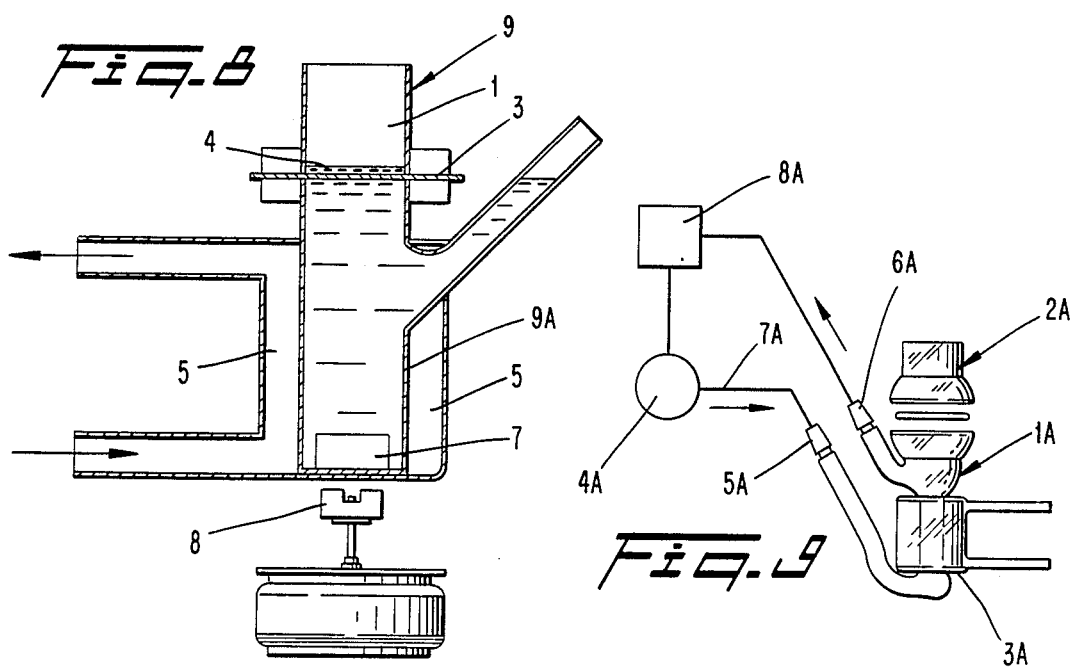

METHODS AND APPARATUS FOR DETERMINING THE RATE OF MOVEMENT OF A STUDY SUBSTANCE THROUGH A MEMBRANE

RELATED INVENTION

Attention is directed to the present inventor's copending U.S. Ser. No. 901,732, filed Aug. 29, 1986 for "Method for In Vitro Determination of Transdermal Absorption".

BACKGROUND AND OBJECTS OF THE INVENTION

The present invention relates to diffusion cells for determining the rate of movement of chemical compounds through natural or synthetic membranes.

In the development of skin-applied drugs, it is desirable to determine the rate at which the drugs, such as systemically bioactive agents, will be absorbed through the human skin. This percutaneous absorption determination can be at least closely approximated through the use of conventional diffusion cells in which a membrane is employed which has absorption characteristics closely paralleling those of living human skin. One conventional type of diffusion cell is depicted in FIG. 8 and basically comprises chambers 1, 2 located on opposite sides of the membrane 3. One chamber 1, i.e., a so-called donor chamber 1 is adapted to receive a dose 4 of the chemical substance under study. The study substance 4 is absorbed through the membrane and enters the other cell 2, i.e., a so-called receptor cell 2. The receptor cell contains a receptor or bathing fluid such as an aqueous solution into which the study substance enters. The receptor fluid is maintained at a constant temperature by thermostatically controlled fluid which circulates through a jacket 5 surrounding the receptor chamber. The receptor fluid bathes the underside of the membrane to closely approximate the condition of living skin tissue. Introduction and removal of the receptor fluid with respect to the receptor chamber is effected through an injection port 6. The receptor fluid is periodically sampled and assayed to determine the concentration of the study substance therein. From that data, the rate of absorption of the study substance can be determined.

A homogenous distribution of the study substance in the receptor fluid is established by means of a stirring bar 7 located in the receptor chamber. The stirring bar is formed of a Teflon-coated magnetic material which is rotated by means of a motor-driven external magnet 8.

The donor chamber is formed by a cell cap 9 which is suitably clamped to the cell body 9A. An O-ring (not shown) is disposed between the cell cap and cell body to effect a fluid seal therebetween.

A shortcoming of the above-described cell involves the inconvenience and time expenditure involved in periodically removing quantities of the receptor fluid for analysis, the removal usually performed manually by means of a syringe.

Another conventional type of diffusion cell is depicted in FIG. 9. That cell is basically similar to the afore-discussed cell in that it comprises a cell body 1A, a cell cap 2A, and a water jacket 3A. A magnetic stirrer (not shown) is disposed in a lower bulbous region 1B of the cell body to which receptor fluid is introduced. Introduction and removal of the receptor fluid is usually acheived by means of a peristaltic pump 4A which is connected to a lower inlet port 5A or an upper outlet port 6A of the receptor cell by means of a flexible tube 7A. Receptor fluid is pumped from the receptor cell to a detector 8A such as a spectrophotometer and from the detector to the inlet port of the receptor cell. The detector provides an essentially continuous monitoring of the receptor fluid, which eliminates the need for the periodic manual removal of the receptor fluid. The peristaltic pump, however, requires the use of flexible tubing which typically contains components, such as plasticizers for example, which can be undesirably desorbed into the receptor fluid. Also, the tubing may absorb some of the study substance thereby adversely affecting the accuracy of the measurements.

It is, therefore, an object of the present invention to minimize or obviate shortcomings of the type discussed above.

Another object is to enable a monitoring of the reactor fluid to be effected without the risk of undesirable materials being desorbed from the tubing into the receptor fluid and without the risk of the study substance being absorbed by the tubing.

A further object is to provide a diffusion cell in which a magnetically driven bar performs both a stirring action and a pumping action, whereby a monitoring can be achieved without the use of a separate pump.

SUMMARY OF THE INVENTION

These objects are achieved by the present invention which involves a diffusion cell for use in determining the absorption rate of a study substance across a permeable membrane. The cell is of the type comprising a cell body adapted to contain a receptor fluid. The cell body is arranged to receive a membrane such that the receptor fluid is adapted to contact one side of the membrane to receive study substance absorbed through the membrane from an opposite side thereof. The cell body defines a receptor chamber adapted to contain the receptor fluid which receives the study substance. The cell body includes an inlet section having an inlet port through which the receptor fluid enters the receptor chamber, and an outlet section including an outlet port through which the receptor fluid exits the receptor chamber. A rotary stirrer is arranged in the outlet section adjacent the outlet port and is adapted to be rotatably driven for rotating the receptor fluid in a manner creating greater fluid pressure in the outlet section than in the inlet section such that the stirrer defines a pump for pumping receptor fluid through the outlet port.

The present invention also relates to a system in which a detector fluid communicates with the outlet and inlet ports for receiving receptor fluid and determining the concentration of study substance in the receptor fluid. In such a case, the stirrer defines the sole means for pumping the receptor fluid to and from the detector.

Preferably, the inlet section comprises an upper section of the receptor chamber, and the outlet section comprises a lower section thereof, with the inlet section communicating with the outlet section through a restricted opening.

Preferably, a by-pass conduit communicates the upper and lower sections independently of the restricted opening. Also, a gas vent communicates with the upper section above the inlet port for venting gas from the receptor chamber.

The present invention also involves method aspects of the above-discussed diffusion cell and system.

THE DRAWINGS

The objects and advantages of the invention will become apparent from the following detailed description of preferred embodiments thereof in connection with the accompanying drawings, in which like numerals designate like elements, and in which:

FIG. 1 is a plan view of a diffusion cell according to the present invention;

FIG. 2 is a vertical sectional view taken through the diffusion cell;

FIG. 3 is a rear elevational view of the diffusion cell;

FIG. 4 is a schematic circuit diagram of a system containing the diffusion cell;

FIG. 5 is a vertical sectional view taken through a modified form of diffusion cell according to the present invention;

FIG. 6 is a plan view of the diffusion cell according to FIG. 5;

FIG. 7 is a rear elevational view of the diffusion cell according to FIG. 5;

FIG. 8 is a schematic view of one type of prior art diffusion cell; and

FIG. 9 is a view of another type of prior art diffusion cell.

DETAILED DESCRIPTION OF PREFERRED EMBODIMENTS OF THE INVENTION

A diffusion cell 10 depicted in FIGS. 1–3, comprises an outside wall 12 which forms a cell body having an internal chamber. The chamber is divided into upper and lower sections 14A, 14B which are of circular horizontal cross-section and are adapted to contain a receptor fluid such as an aqueous solution. The upper section 14A communicates with a horizontal passage 16 which provides access to the exterior. A flange 18 surrounds an open end of the passage 16 and includes a groove 20 adapted to receive an O-ring seal 22.

A cell cap 24 is adapted to be connected to the cell body by means of a suitable clamp 26, such as that described in U.S. Pat. No. 2,397,438, for example, with a membrane 28 clamped between the cell body and the O-ring seal 22 so as to lie across the inlet of the passage 16. The membrane can be of any suitable type such as that disclosed in the inventor's afore-mentioned related U.S. application Ser. No. 901,732. Hence, a study substance, such as a medicinal ointment can be applied to the external side of the membrane 28, i.e., to the cell cap side of the membrane opposite the passage 16.

The other side of the membrane, i.e., the cell body side, is bathed by the receptor fluid which fills the chamber 14. The study substance is absorbed through the membrane and enters the receptor fluid which is initially introduced into the chamber 14 by means of an ingress port 30. That port 30 is continually exposed to atmosphere for exhausting gas bubbles from the chamber 14 and maintaining the solution within the chamber at atmospheric pressure. By exhausting the bubbles, it is assured that the bubbles will not contact and dehydrate the membrane and interfere with the transfer process.

The upper section 14A of the receptor chamber 14 constitutes a fluid inlet section and the lower section 14B constitutes a fluid outlet section. Thus, the upper section 14A includes a fluid inlet port 32 which opens into the upper section 14a for conducting a flow of receptor fluid to the upper section 14A. The lower section 14B includes a fluid outlet port 36 for discharging the receptor fluid from the chamber 14.

The lower section 14B communicates with the upper section 14A by means of a reduced opening 34 which preferably has a diameter no greater than, and most preferably less than, one-half of the diameter of the lower section 14B, and a height no greater than, and most preferably less than, the height of the lower section 14B. The diameter of the upper section 14A is preferably somewhat less than the diameter of the lower section 14B.

Situated in the lower section 14B is a stirrer element 35 which comprises a conventional teflon-coated magnetic material and is of generally solid cylindrical configuration. The stirrer extends at least as high as an uppermost portion of the outlet port. The stirrer element 37 is adapted to be rotated by a conventional motor-driven magnet 38 (FIG. 4) in order to produce a rotation of the receptor fluid.

It has been found by the present inventor that by configuring the chamber 14 to produce a substantially greater speed of rotation of the receptor fluid in the lower section 14B than in the upper section 14A, and by employing the port 36 as an outlet port, the stirrer 35 will function as a pump for circulating receptor fluid outwardly through the outlet port 36, through a fluid circuit, and back into the chamber 14 via the inlet port 32, thereby eliminating the need for a separate external pump.

By making the opening 34 of appreciably less horizontal cross-sectional area than the lower section 14B, the amount of rotary action imparted by the stirrer 35 to the receptor fluid in the upper section 14A is significantly less than that imparted to the receptor fluid in the lower section 14B. Hence, the receptor fluid at the periphery of the lower section will rotate faster than (and in the same direction as) the receptor fluid at the periphery of the upper section 14A. Consequently, the fluid pressure created by centrifugal force at the periphery of the lower section 14B will be greater than the fluid pressure created by centrifugal force at the periphery of the upper section 14A. There will thus be induced a circulation of receptor fluid through the outlet port 36, then through the fluid circuit, and then back into the receptor chamber 14 through the inlet port 32, solely by means of the pressure difference created by the rotary stirrer 35.

By placing a computerized detector such as a conventional spectrophotometer 40 in the fluid circuit, an analysis of the receptor fluid can be performed to determine the rate at which the study compound is absorbed through the membrane. That is, the pumping action produced by the stirrer circulates receptor fluid from the outlet port 36 to an inlet of the detector and then from an outlet of the detector to the inlet port 32. The pumping action and detector analysis can be effected periodically, or continuously if desired.

Since no separate external pump is needed, capital costs and maintenance expenditures are reduced. Furthermore, the problems created by the flexible tubing associated with peristaltic pumps, i.e., the absorption of study compound into the tubing and/or the desorption of contaminants from the tubing into the receptor fluid are avoided. Thus, the conduits forming the fluid circuitry can be made of any suitable material, such as glass or Teflon, for example, which will not react with the receptor fluid or the study substance.

The cell body and cell cap 24 are formed of a material which will not react with or absorb the receptor fluid and study substance, such as glass or Teflon for example.

In order to enhance the amount of fluid circulation between the upper and lower sections, a bypass conduit 42 can be extended between an upper end of the upper section 14A and a lower end of the lower section 14B. This feature also increases the stirring action at the surface of the membrane.

Although the passage 16 has been disclosed as extending horizontally, i.e., perpendicularly to the central axis of the opening 34, it is possible to orient that passage vertically or inclined at an acute angle relative to vertical.

The temperature of the receptor fluid can be maintained at a desired temperature in any suitable manner such as by heating the environment in which the cell is located, interposing a heater in the fluid circuit, or providing a conventional temperature control jacket 50 around the cell as depicted in FIGS. 5–7. A fluid maintained at a prescribed temperature is continuously circulated through the space 52 formed between the wall 12 and the jacket 50. That fluid is introduced through an ingress port 54 and exits via an egress port 56.

It will be apparent that the present invention provides a diffusion cell which eliminates the need for manual removal of the receptor fluid and also eliminates the need for tubing of the sort which may result in study compound being absorbed into the tubing or contaminants desorbed from the tubing into the reactor fluid. The invention provides those advantages without the need for a separate pump, since the typically employed stirrer is able to achieve the required pumping action.

Although the present invention has been described in connection with preferred embodiments thereof, it will be appreciated by those skilled in the art that modifications, substitutions, additions and deletions not specifically described may be made without departing from the spirit and scope of the invention as defined in the appended claims.

What I claim is:

1. A system for determining the adsorption rate of a study substance through a permeable membrane, comprising:
   a cell body defining a receptor chamber containing receptor fluid, said cell body including an upper section into which receptor fluid enters said receptor chamber, and a lower section from which receptor fluid exits said receptor chamber, a fluid inlet port communicating with said upper section, a fluid outlet port communicating with said lower section, a restricted opening communicating said upper section with said lower section, said restricted opening having a smaller cross-section than said lower section, said outlet port arranged tangentially relative to said lower section,
   rotary stirrer means arranged in said lower section adjacent said outlet port, said stirrer means arranged in said lower section to extend at least as high as an uppermost portion of said outlet port,
   a permeable membrane,
   means for securing said membrane to said cell body such that one side of said membrane contacts receptor fluid in said receptor chamber and the other side of said membrane is adapted to receive study substance such that the study substance is absorbed through said membrane and enters the receptor fluid,
   a detector communicating with said outlet and inlet ports for determining the concentration of study substance in receptor fluid received from said outlet port, and
   means for rotating said stirrer means to rotate the receptor fluid in said receptor chamber in a manner creating greater fluid pressure at said outlet port than at said inlet port for pumping receptor fluid through said outlet port, through said detector, and then back into said receptor chamber through said inlet port, said stirrer means constituting the sole means for circulating receptor fluid between said cell body and said detector.

2. A system according to claim 1, wherein said restricted opening has a height shorter than a height of said lower section.

3. A system according to claim 2, wherein said height of said restricted opening is no greater than one-half said height of said lower section.

4. A system according to claim 1, wherein said restricted opening has a cross-sectional area which is no greater than one-half the cross-sectional area of said lower section.

5. A system according to claim 1 including a by-pass conduit communicating said upper and lower sections independently of said restricted opening, said by-pass conduit oriented to direct receptor fluid from said lower section toward said permeable membrane.

6. A system according to claim 1, wherein said means for rotating said stirrer comprises a motor driven magnet.

7. A system according to claim 1 including a cell cap defining a donor chamber including a first passage, and said cell body including a second passage, said cell cap being removably mounted to said cell body such that said first and second passages are in communication with one another and a membrane is adapted to be clamped therebetween.

8. A system according to claim 7, wherein said passages extend substantially horizontally.

9. A system according to claim 7, wherein said passages extend at an acute angle relative to vertical.

10. A system according to claim 7 including a jacket surrounding at least a portion of said receptor chamber and defining a fluid chamber including ingress and egress openings for circulating a temperature control medium through said fluid chamber.

11. A system according to claim 7 including a gas vent communicating with said upper section above said inlet port for venting gas from said receptor chamber.

12. A diffusion cell for use in determining the absorption rate of a study substance through a permeable membrane, said cell being of the type comprising a cell body adapted to contain a receptor fluid and means for receiving the membrane such that the receptor fluid is adapted to contact one side of the membrane to receive study substance absorbed through the membrane from an opposite side of the membrane, said cell body defining a receptor chamber adapted to contain the receptor fluid which receives the study substance, said cell body including an upper section having an inlet port through which the receptor fluid enters said receptor chamber, and a lower section including an outlet port from which the receptor fluid exits said receptor chamber, and rotary stirrer means arranged in said lower section adjacent said outlet port and adapted to be rotatably driven for rotating the receptor fluid in a manner creating greater fluid pressure in said lower section than in said upper section such that said stirrer means defines a pump for pumping receptor fluid through said outlet port, a restricted opening communicating said upper section with said lower section, said restricted opening having a smaller cross-section than said lower section, said outlet port being arranged tangentially relative to said lower section, and said stirrer means arranged in said lower section to extend at least as high as an uppermost portion of said outlet port.

13. A diffusion cell according to claim 12, wherein said restricted opening has a height shorter than a height of said lower section.

14. A diffusion cell according to claim 13, wherein said height of said restricted opening is no greater than one-half said height of said lower section.

15. A diffusion cell according to claim 12, wherein said restricted opening has a cross-sectional area which is no greater than one-half the cross-sectional area of said lower section.

16. A diffusion cell according to claim 12, wherein said stirrer means comprises a magnetic bar adapted to be rotated by a motor driven magnet, said restricted opening having a cross-sectional area less than one-half the cross-sectional area of said lower section, said restricted opening having a height no greater than one-half the height of said lower section.

17. A diffusion cell according to claim 12 including a by-pass conduit communicating said upper and lower sections independently of said restricted opening, said by-pass conduit oriented to direct receptor fluid from said lower section toward said membrane-receiving means.

18. A diffusion cell according to claim 12, wherein said stirrer means comprises a magnetic bar adapted to be rotated by a motor driven magnet.

19. A diffusion cell according to claim 12, including a cell cap defining a donor chamber including a first passage, and said cell body including a second passage, said cell cap being removably mounted to said cell body such that said first and second passages are in communication with one another and a the membrane is adapted to be clamped therebetween.

20. A diffusion cell according to claim 19, wherein said passages extend substantially horizontally.

21. A diffusion cell according to claim 19, wherein said passages extend at an acute angle relative to vertical.

22. A diffusion cell according to claim 19 including a jacket surrounding at least a portion of said receptor chamber and defining a fluid chamber including ingress and egress openings for circulating a temperature control medium through said fluid chamber.

23. A diffusion cell according to claim 19 including a gas vent communicating with said upper section above said inlet port for venting gas from said receptor chamber.

24. A method for determining the absorption rate of a study substance through a membrane, said method comprising the steps of:
providing a cell body having a receptor chamber therein which contains receptor fluid, said chamber including an upper section having a fluid inlet port, a lower section having a fluid outlet port, and a rotary stirrer positioned in said lower section adjacent said fluid outlet port, a restricted opening communicating said upper section with said lower section, said restricted opening having a smaller cross-section than said lower section, said outlet port arranged tangentially relative to said lower section, said stirrer means arranged in said lower section to extend at least as high as an uppermost portion of said outlet port,
arranging a membrane on said cell body such that one side of said membrane communicates with said receptor chamber and is contacted by receptor fluid therein such that study substance which is absorbed through said membrane from an opposite side thereof enters the receptor fluid,
placing said outlet and inlet ports in fluid communication with a detector for determining the concentration of study substance in the receptor fluid, and
circulating receptor fluid from said cell body to said detector and back to said cell body solely by rotating said stirrer to rotate the receptor fluid in said receptor chamber in a manner creating greater fluid pressure in said lower section than in said upper section such that said stirrer draws receptor fluid into said lower section through said restricted opening and then pumps receptor fluid tangentially outwardly through said tangential outlet port, through said detector, and back into said upper section through said inlet port.

25. A method according to claim 24 including the step of circulating receptor fluid from said lower section to said upper section through a by-pass conduit separate from said restricted opening, and directing fluid from said by-pass conduit toward said membrane.

26. A method according to claim 24, wherein said rotating step comprises rotating said stirrer by a motor-driven magnet.

27. A method according to claim 24 including the step of venting gas bubbles from said upper section to atmosphere.

* * * * *